US010517556B2

(12) United States Patent
Chen et al.

(10) Patent No.: US 10,517,556 B2
(45) Date of Patent: Dec. 31, 2019

(54) SYSTEM AND METHOD FOR TEMPORAL FIDELITY ENHANCED MEDICAL IMAGING USING TEMPORAL DECONVOLUTION

(71) Applicant: Wisconsin Alumni Research Foundation, Madison, WI (US)

(72) Inventors: Guang-Hong Chen, Madison, WI (US); Jie Tang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 143 days.

(21) Appl. No.: 13/763,593

(22) Filed: Feb. 8, 2013

(65) Prior Publication Data

US 2014/0228674 A1 Aug. 14, 2014

(51) Int. Cl.
*A61B 5/05* (2006.01)
*A61B 6/00* (2006.01)
(Continued)

(52) U.S. Cl.
CPC .......... *A61B 6/481* (2013.01); *A61B 5/0037* (2013.01); *A61B 5/7203* (2013.01); *A61B 6/025* (2013.01); *A61B 6/032* (2013.01); *A61B 6/4085* (2013.01); *A61B 6/4441* (2013.01); *A61B 6/461* (2013.01); *A61B 6/467* (2013.01); *A61B 6/486* (2013.01); *A61B 6/507* (2013.01); *A61B 6/52* (2013.01); *A61B 6/5217* (2013.01); *A61B 6/5258* (2013.01); *A61B 6/54* (2013.01); *G01R 33/5608* (2013.01); *A61B 5/0059* (2013.01);
(Continued)

(58) Field of Classification Search
None
See application file for complete search history.

(56) References Cited

U.S. PATENT DOCUMENTS

2010/0106007 A1\* 4/2010 Wacker et al. ............... 600/420
2011/0133735 A1\* 6/2011 Yokosawa et al. ........... 324/307
(Continued)

OTHER PUBLICATIONS

Fieselmann et al. (Interventional 4-D C-Arm CT Perfusion Imaging Using Interleaved Scanning and Partial Reconstruction Interpolation; IEEE transaction on medical imaging, vol. 31, No. 1, Apr. 2012).*

(Continued)

*Primary Examiner* — Thomas J Hong
*Assistant Examiner* — Shahdeep Mohammed
(74) *Attorney, Agent, or Firm* — Quarles & Brady LLP

(57) ABSTRACT

A method for increasing the temporal fidelity, increasing the temporal sampling density, and/or reducing the temporal noise of a series of image frames obtained with a medical imaging system is provided. The image frames are acquired with the medical imaging system. The medical imaging system may be, for example, an x-ray C-arm imaging system. A window function that is representative of a temporal fidelity window is selected and used to temporally deconvolve the image frames using a minimization technique. A temporal sampling density may also be selected and used in the temporal deconvolution. The resultant deconvolved image frames have a higher temporal fidelity to a time-varying image contrast depicted in the acquired image frames, and may also have an increased temporal sampling density and/or reduced temporal noise.

11 Claims, 5 Drawing Sheets

(51) Int. Cl.
| | |
|---|---|
| A61B 5/00 | (2006.01) |
| A61B 6/02 | (2006.01) |
| A61B 6/03 | (2006.01) |
| G01R 33/56 | (2006.01) |
| A61B 5/055 | (2006.01) |
| G01R 33/563 | (2006.01) |

(52) U.S. Cl.
CPC ............ *A61B 5/055* (2013.01); *A61B 5/7292* (2013.01); *G01R 33/5601* (2013.01); *G01R 33/5602* (2013.01); *G01R 33/56325* (2013.01); *G01R 33/56366* (2013.01)

(56) References Cited

U.S. PATENT DOCUMENTS

| | | | | |
|---|---|---|---|---|
| 2011/0241670 | A1* | 10/2011 | Lai | G01R 33/5611 324/309 |
| 2013/0051644 | A1* | 2/2013 | Nett | G06T 11/008 382/131 |
| 2013/0211245 | A1* | 8/2013 | Vembar | A61B 6/032 600/428 |

OTHER PUBLICATIONS

Montes et al. ("Low-Noise Dynamic Reconstruction for X-Ray Tomographic Perfusion Studies Using Low Sampling Rates"; International Journal of Biomedical Imaging, vol. 2009).*

Hom et al. ("an adaptive image deconvolution algorithm with application of multi-frame and three dimensional data"; J OPT Soc Am A Opt Image Sci Vis, Jun. 2007).*

Eastwood et al. ("CT perfusion scanning with deconvolution analysis: pilot study in patients with acute middle cerebral artery stroke"; Radiology, vol. 222; Jan. 2002).*

Adams, et al., Guidelines for the Early Management of Patients with Ischemic Stroke, 2005 Guidelines Update, A Scientific Statement from the Stroke Council of the American Heart Association/American Stroke Association, Stroke, 2005, 36:916-923.

Adams, et al., Guidelines for the Early Management of Adults with Ischemic Stroke, A Guideline from the American Heart Association/American Stroke Association Stroke Council, Stroke, 2007, 38:1655-1711.

Adams, et al., Guidelines for the Early Management of Adults with Ischemic Stroke, A Guideline from the American Heart Association/American Stroke Association Stroke Council, Circulation, 2007, 115:e478-e534.

Adams, et al., Guidelines for the Early Management of Patients with Ischemic Stroke, A Scientific Statement from the Stroke Council of the American Stroke Association, Stroke, 2003, 34:1056-1083.

Fieselmann, et al., Interventional 4-D C-Arm CT Perfusion Imaging Using Interleaved Scanning and Partial Reconstruction Interpolation, IEEE Transactions on Medical Imaging, 2012, 31(4):892-906.

Ganguly, et al., Evaluating the Feasibility of C-Arm CT for Brain Perfusion Imaging: An In Vitro Study, Proc. of SPIE, 2010, 7625:76250K-1-76250K-8.

Ganguly, et al., Cerebral CT Perfusion Using an Interventional C-Arm Imaging System: Cerebral Blood Flow Measurements, AJNR Am. J. Neuroradiol., 2011, 32:1525-1531.

Konstas, et al., Theoretic Basis and Technical Implementations of CT Perfusion in Acute Ischemic Stroke, Part 1: Theoretic Basis, AJNR Am. J. Neuroradiol., 2009, 30:662-668.

Konstas, et al., Theoretic Basis and Technical Implementations of CT Perfusion in Acute Ischemic Stroke, Part 2: Technical Implementations, AJNR Am. J. Neuroradiol., 2009, 30:885-892.

Weimar, et al., Age and National Institutes of Health Stroke Scale Score Within 6 Hours After Onset Are Accurate Predictors of Outcome After Cerebral Ischemia, Stroke, 2004, 35:158-162.

Yin, et al., Bregman Iterative Algorithms for I1-Minimization with Applications to Compressed Sensing, SIAM Journal on Imaging Sciences, 2008, 1(1):143-168.

* cited by examiner

SYSTEM AND METHOD FOR TEMPORAL FIDELITY ENHANCED MEDICAL IMAGING USING TEMPORAL DECONVOLUTION

STATEMENT REGARDING FEDERALLY SPONSORED RESEARCH

This invention was made with government support under EB009699 awarded by the National Institutes of Health. The government has certain rights in the invention.

BACKGROUND OF THE INVENTION

The field of the invention is systems and methods for medical imaging. More particularly, the invention relates to systems and methods for improving fidelity of contrast dynamics in medical imaging modalities including diagnostic computed tomography, x-ray C-arm imaging, x-ray tomosynthesis imaging, ultrasound imaging, optical imaging, and magnetic resonance imaging.

The outcome of managing ischemic stroke critically depends on the time spent on diagnosis and interventions. To identify salvageable tissues of stroke patients, either x-ray computed tomography ("CT") perfusion or magnetic resonance imaging ("MRI") perfusion imaging is commonly ordered. Unfortunately, it often takes hours to schedule and perform perfusion imaging studies. The transportation of diagnostic patients between the imaging and interventional suites not only adds burden to work flow, but it also increases treatment time in the already very tight time window for stroke treatment, which is usually within six hours from onset of the stroke.

Image-guided interventions are normally conducted in an angiographic suite; thus, if the perfusion information can be obtained with an angiographic C-arm cone beam CT ("CBCT") system, the stroke patients may be directly triaged to the angiographic suite to minimize the diagnostic time before interventions. It would therefore be desirable to be able to perform perfusion imaging with a C-arm CBCT system.

Flat-panel detector based C-arm CBCT systems, however, are significantly different from sub-second rotation, slip-ring gantry based diagnostic CT systems. C-arm CBCT has a prolonged data acquisition time that is limited by detector readout speed, mechanical stability of the C-arm gantry, and radiation safety requirements. As a result, typically less than ten time frames can be acquired within a minute of data acquisition time. For each time frame, the temporal resolution is limited to 3-5 seconds. Therefore, there are two major challenges in current attempts to achieving C-arm cone-beam CT perfusion. First, temporal resolution of 3-5 seconds is too poor to accurately record and delineate contrast dynamics. Second, the total number of acquired time frames is too few to enable estimation of perfusion information from time density curves. In addition to future hardware upgrades that may enable faster data acquisitions using the C-arm gantry, it would be highly desirable to develop technology that would enable perfusion imaging using the current hardware acquisition systems.

An interleaved scan method was proposed to improve the perfusion performance of C-arm CBCT systems. In this method, two perfusion scans are performed, with the second perfusion scan having a different x-ray delay time after contrast injection. For example, the contrast injection in the second scan may be delayed by three seconds relative to the first scan. Assuming the contrast dynamics are identical with the same contrast injection protocol, the available time frames can be doubled with this method.

There are limitations for the interleaved CBCT perfusion image method, however. First, the assumption made by this method—that contrast dynamics are repeatable in cerebral perfusion studies—has never been validated. Second, because two perfusion scans are required, both the contrast dose and the radiation dose are doubled. In addition, the data acquisition time are also doubled. None of these increases are desirable for improved patient care. Another limitation of the interleaved method is that the temporal resolution of each time frame is still the same as with conventional methods, even though the available time frames are doubled. Thus, the interleaved method only partially addresses the temporal sampling problems of C-arm CBCT perfusion imaging and does not address the temporal resolution problems.

It would therefore be desirable to provide systems and methods for medical imaging in which the fidelity of contrast dynamics and kinematics is enhanced relative to currently available technologies.

SUMMARY OF THE INVENTION

The present invention overcomes the aforementioned drawbacks by providing a method for enhancing the temporal fidelity of contrast dynamics and kinematics of a series of image frames obtained with a medical imaging system using a temporal deconvolution technique.

It is an aspect of the invention to provide a method for increasing a temporal fidelity of a series of image frames obtained with a medical imaging system. The method includes acquiring a series of image frames depicting a time-varying image contrast in a subject using the medical imaging system. A window function that is representative of a temporal fidelity window is then selected, and another series of image frames having an increased temporal fidelity to the time-varying image contrast as compared to the acquired series of image frames is produced. The another series of image frames is produced by performing a temporal deconvolution on the acquired series of image frames acquired using the selected window function.

It is another aspect of the invention to provide a method for increasing a temporal sampling density of a series of image frames obtained with a medical imaging system. The method includes acquiring a series of image frames at a first temporal sampling density using the medical imaging system. A window function that is representative of a temporal fidelity window and a second temporal sampling density that is higher than the first temporal sampling density are then selected. Another series of image frames having the second temporal sampling density is produced by performing a temporal deconvolution of the acquired series of image frames using the selected window function and the second temporal sampling density.

It is yet another aspect of the invention to provide a method for reducing temporal noise in a series of image frames obtained with a medical imaging system. The method includes acquiring a series of image frames having a level of temporal noise using the medical imaging system. A window function that is representative of a temporal fidelity window and a temporal sampling density are selected. Another series of image frames having reduced temporal noise as compared to the acquired series of image frames is produced by performing a temporal deconvolution on the acquired series of image frames using the selected window function and temporal sampling density.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
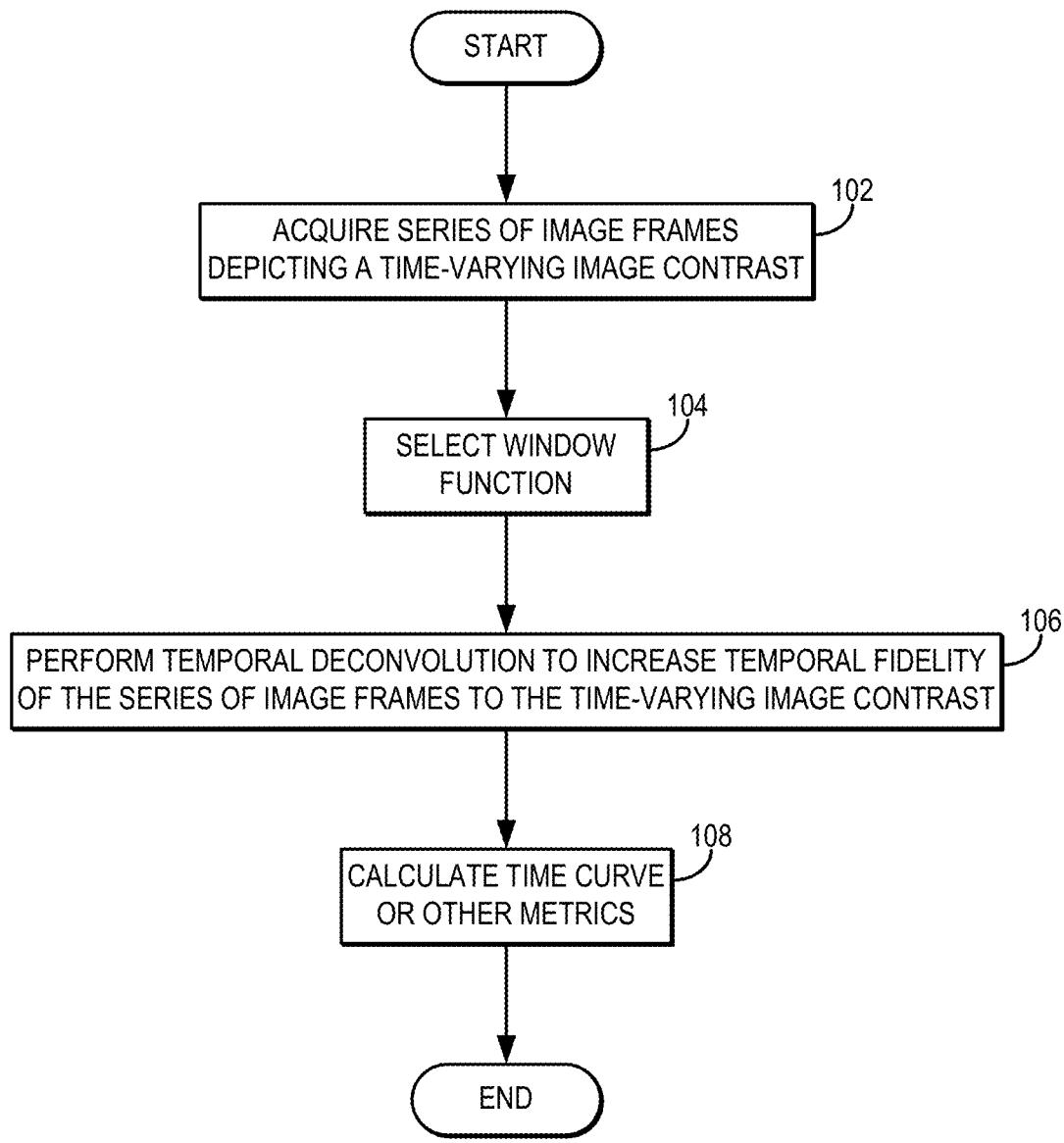
FIG. 1 is a flowchart setting forth the steps of an example of a method for improving the temporal fidelity of a series of time frames using temporal deconvolution techniques.

A temporal deconvolution technique for increasing the temporal fidelity of contrast dynamics in medical imaging applications is provided. In general, the temporal fidelity of the contrast dynamics of a time series of images may refer to the degree to which the computed time enhancement curve, or other contrast dynamics or kinematics model computed from the images, reproduces the state and behavior of the contrast dynamics occurring in the subject during imaging. Contrast dynamics may refer to the dynamics of an exogenous contrast agent administered to the subject, or to the dynamics of an inherent contrast, such as the relaxation of magnetization in a magnetic resonance imaging session. The method of the present invention may also be used to increase the temporal sampling density of a series of image frames. By way of example, the method of the present invention may be used to increase the fidelity of contrast dynamics and to increase the temporal sampling density of a time series of image frames obtained with a medical imaging system, such as a diagnostic computed tomography ("CT") system, a C-arm x-ray imaging system, an x-ray tomosynthesis imaging system, an ultrasound system, an optical imaging system, or a magnetic resonance imaging ("MRI") system.

Due to hardware limitations, the data acquisition speed of current C-arm cone beam computed tomography ("CBCT") systems is relatively slow. For instance, it is common that only seven time frames are available for a forty-five second perfusion study. Using the method of the present invention, however, temporal enhancement curves in C-arm CBCT perfusion studies can be recovered. The temporal deconvolution method of the present invention makes use of a constrained optimization problem to improve the temporal resolution of the acquired time frames.

In CBCT perfusion studies, a tomographic reconstruction procedure tends to average out the temporal dynamics of the contrast materials in the blood stream. This averaging procedure can be modeled as a convolution of the ground truth contrast dynamics with a temporal window function. Although this window function may have dependence on the weighting function used in the conventional filtered back-projection ("FBP") reconstruction (e.g., Parker weighting), it is a reasonable approximation to simply use a box-car sharp window function. This box-car window function is provided as an example, and other window functions may be readily implemented instead. The box-car sharp window function can be written as, $$\prod\left(\frac{t-t'_i}{T}\right); \quad (1)$$

and defined as, $$\prod(x) = \begin{cases} 0 & \text{if } |x| > 1/2 \\ 1/2 & \text{if } |x| = 1/2 \\ 1 & \text{if } |x| < 1/2. \end{cases} \quad (2)$$

For each voxel in a series of time frames obtained in a perfusion imaging study, or other time-resolved study, such as a time-resolved angiographic study, there is a corresponding temporal density curve, $C(t)$. The working assumption described above can thus be summarized in the following equation:

$$C_m(t'_i) = C(t) \otimes \prod\left(\frac{t-t'_i}{T}\right) \quad (3)$$

where $C_m(t'_i)$ ($i=1, 2, \ldots, N$) denotes the measured data points at time $t'_i$, which are acquired from each scan in the time period $$\left[t'_i - \frac{T}{2}, t'_i + \frac{T}{2}\right];$$

and N is the total number of time frames acquired in the imaging session. Although the time density curve, $C(t)$, has a continuous form, it is generally digitized in practice. Thus, let $C(t_i)$ denote the discrete form of the time density curve, with $$t_i = k\Delta t \quad (4);$$

where $k=0, 1, 2, \ldots, M$ and $\Delta t$ is the sampling interval in the digitization. By way of example, it is numerically sufficient to sample the deconvolved time density curve using a sampling interval of $\Delta t=0.5$ seconds. The sampling interval, $\Delta t$, used in the window function can be selected to control the temporal sampling density.

In this discrete form, the convolution model in time-resolved CBCT contrast dynamics is given by $$C_m = AC; \quad (5)$$

where $$C_m = \begin{bmatrix} C_m(t'_1) \\ C_m(t'_2) \\ \vdots \\ C_m(t'_N) \end{bmatrix}; \quad (6)$$

-continued $$A = \begin{bmatrix} \Pi\left(\frac{t_1 - t'_1}{T}\right) & \Pi\left(\frac{t_2 - t'_1}{T}\right) & \cdots & \Pi\left(\frac{t_M - t'_1}{T}\right) \\ \Pi\left(\frac{t_1 - t'_2}{T}\right) & \Pi\left(\frac{t_2 - t'_2}{T}\right) & \cdots & \Pi\left(\frac{t_M - t'_2}{T}\right) \\ \vdots & \vdots & \ddots & \vdots \\ \Pi\left(\frac{t_1 - t'_N}{T}\right) & \Pi\left(\frac{t_2 - t'_N}{T}\right) & \cdots & \Pi\left(\frac{t_M - t'_N}{T}\right) \end{bmatrix}; \quad (7)$$

$$C = \begin{bmatrix} C(t_1) \\ C(t_2) \\ \vdots \\ C(t_M) \end{bmatrix}. \quad (8)$$

Based on this working assumption and the known data acquisition time, $t'_i$, it is a teaching of the present invention that a numerical deconvolution procedure can be performed to reconstruct the assumed true time density curve, $C(t_i)$, from the acquired data points, $C_m(t'_i)$. Due to the temporal sampling challenge, however, Fourier based singular value decomposition ("SVD") methods are not appropriate to perform the needed deconvolution. As a consequence, an optimization-based method is provided to solve the deconvolution problem in Eqn. (5), as will now be described.

The deconvolution problem in Eqn. (5) is formulated as a numerical inverse problem, and the appropriate regularization schemes can be applied to stably perform the deconvolution iteratively. Note that even with a small number of data points, such as seven (N=7), the deconvolution can be used to obtain the corresponding value at an arbitrary time point based on an input of the only seven measured data points. In effect, this approach has the same functionality of increasing the sampling density by a temporal interpolation method, but it is fundamentally different from other known interpolation methods, which rely on deriving information from nearby data points. There is a fundamental difference between the proposed method and conventional interpolation methods. Notably, interpolation methods assume all measurements are accurate, which is not true in C-arm CBCT on account of the low temporal resolution. The temporal deconvolution method of the present invention models the inaccuracies in measurement of contrast enhancement at the acquired time frames that are introduced by the low temporal resolution; thus, the method allows for more accurate recovery of contrast dynamic curves, thereby allowing for more accurate perfusion maps.

Generally, the problem is to recover the time density curves, C, using the known window functions, A, and the acquired data, $C_m$. This discrete deconvolution problem is a highly ill-posed problem with possibly infinitely many solutions. One potential solution to this problem is a step function, in which each step covers the data acquisition time and whose values correspond to the mean value measured within that data acquisition time. Because the time density curves in a real perfusion experiment are usually smooth, this prior knowledge can be incorporated to formulate the deconvolution as the following constrained optimization problem:

$$C = \underset{C}{\operatorname{argmin}}\{\|\nabla C\|_2\} \quad (9)$$

such that $C_m = AC;$ where $$\nabla C_i = C_{i+1} - C_i. \quad (10)$$

A numerical method may be used to solve the constrained minimization problem represented in Eqn. (9). For instance, the problem can be converted into an unconstrained minimization problem by adding a quadratic penalty term:

$$C = \underset{C}{\operatorname{argmin}}\{\|\nabla C\|_2^2 + \lambda\|C_m - AC\|_2^2\}; \quad (11)$$

which is a minimization problem for a quadratic form. The minimization problem represented in Eqn. (11) can be solved by many existing optimization methods, such as a conjugate gradient ("CG") method. Additionally, the minimization problem represented in Eqn. (11) can be generalized from the quadratic form to a p-norm by replacing the $\|\nabla C\|_2^2$ term with $\|\nabla C\|_p^p$, where in general p is on the range [1,2].

Referring now to FIG. 1, a flowchart setting forth the steps of an example of a method for increasing the temporal fidelity of a series of time frames obtained with a medical imaging system is illustrated. The method begins with acquiring the series of time frames, as indicated at step 102. By way of example, the time frames may be obtained with a C-arm CBCT system; however, the time frames can also be acquired with an MRI system or other suitable medical imaging system. The series of time frames, or image frames, depict a time-varying image contrast of the subject. This time-varying image contrast may be from an exogenous contrast agent administered to the subject, or may be an inherent image contrast, such as one related to the relaxation of magnetization in magnetic resonance imaging. Next, a window function that is representative of a temporal fidelity window is selected, as indicated at step 104. As described above, the window function may be a box-car sharp window function, or other suitable window function. Using the acquired time frames and the selected window function, a temporal deconvolution is used to improve the temporal fidelity of the acquired time frames, as indicated at step 106. Particularly, the temporal deconvolution includes solving a minimization problem, whether constrained or unconstrained. The improved image frames have increased temporal fidelity to the time-varying contrast in the subject than do the original image frames. As indicated at step 108, after the temporal fidelity of the time frames has been increased, a temporal enhancement curve, or other metrics, can be calculated with increased accuracy as compared to the original, lower temporal fidelity time frames.

By way of example, the temporal deconvolution method of the present invention may be used to recover time density curves to enable C-arm CBCT perfusion studies. The time density curves are recovered by solving a deconvolution problem with very few measurements. This formulated problem is a highly ill-posed problem, thus a regularization term is introduced, and the problem becomes a constrained minimization problem. A constrained minimization problem can be converted to an unconstrained problem, using a Lagrange multiplier, for example, and then solved to get a solution that well approximates the solutions in the original constrained minimization problem. Alternatively, a mathematically exact solution can be found for the constrained minimization problem using an appropriate numerical method, such as the Bregman iterative algorithm or an augmented Lagrangian multiplier method.

Figure 2:
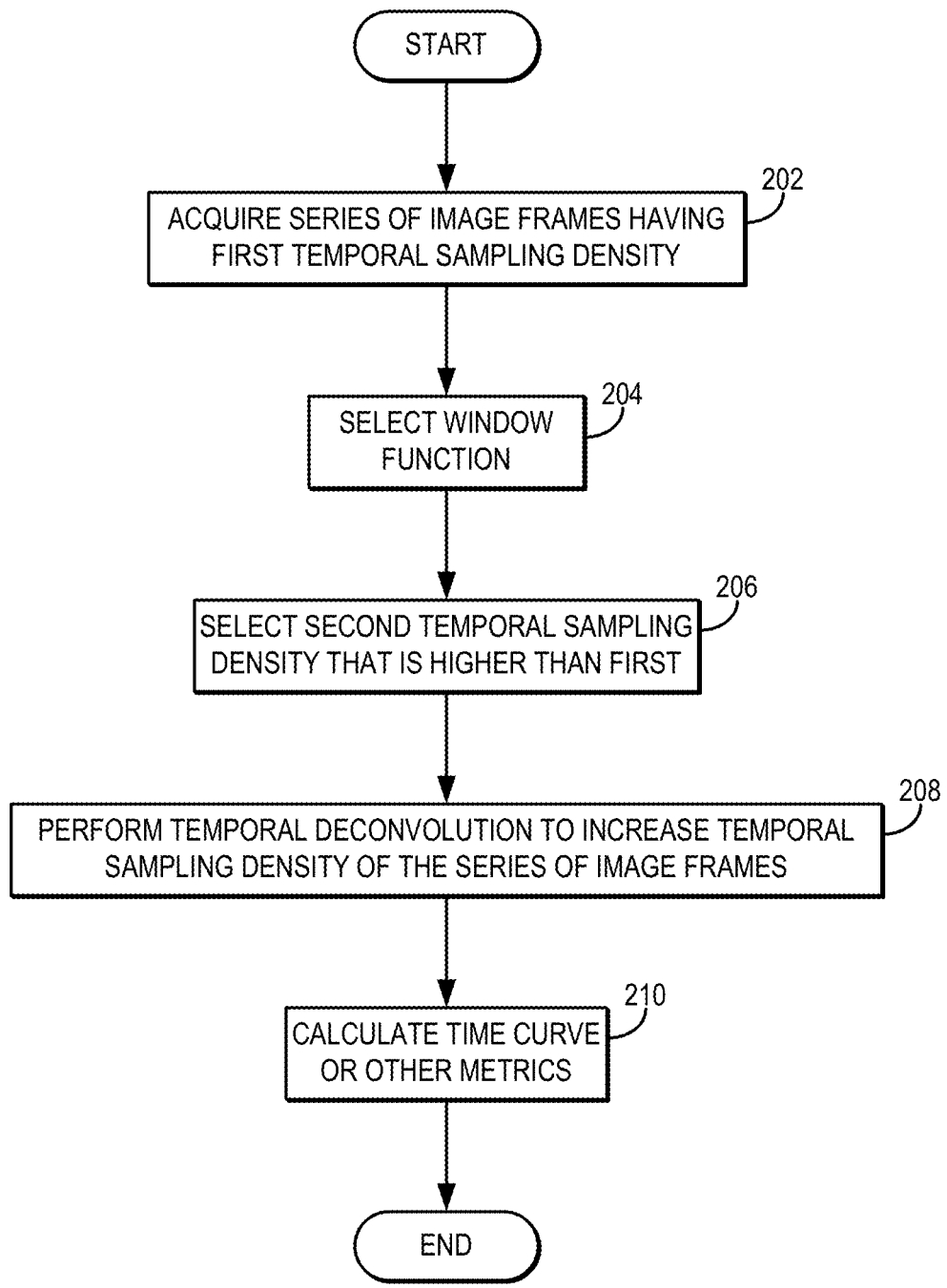
FIG. 2 is a flowchart setting forth the steps of an example of a method for improving the temporal sampling density of a series of time frames using temporal deconvolution techniques

Referring now to FIG. 2, a flowchart setting forth the steps of an example of a method for increasing the temporal sampling density of a series of time frames obtained with a medical imaging system is illustrated. The method begins with acquiring the series of time frames, as indicated at step 202. By way of example, the time frames may be obtained with a C-arm CBCT system; however, the time frames can also be acquired with an MRI system or other suitable medical imaging system. Next, a window function that is representative of a temporal fidelity window is selected, as indicated at step 204. As described above, the window function may be a box-car sharp window function, or other suitable window function. A temporal sampling density that is higher than the temporal sampling density at which the original image frames were acquired is selected, as indicated at step 206. Using the acquired time frames, the selected window function, and the selected temporal sampling density, a temporal deconvolution is used to improve the temporal sampling density of the acquired time frames, as indicated at step 208. Particularly, the temporal deconvolution includes solving a minimization problem, whether constrained or unconstrained. As indicated at step 210, after the temporal sampling density of the time frames has been increased, a temporal enhancement curve, or other metrics, can be calculated with increased accuracy as compared to the original time frames.

Figure 3:
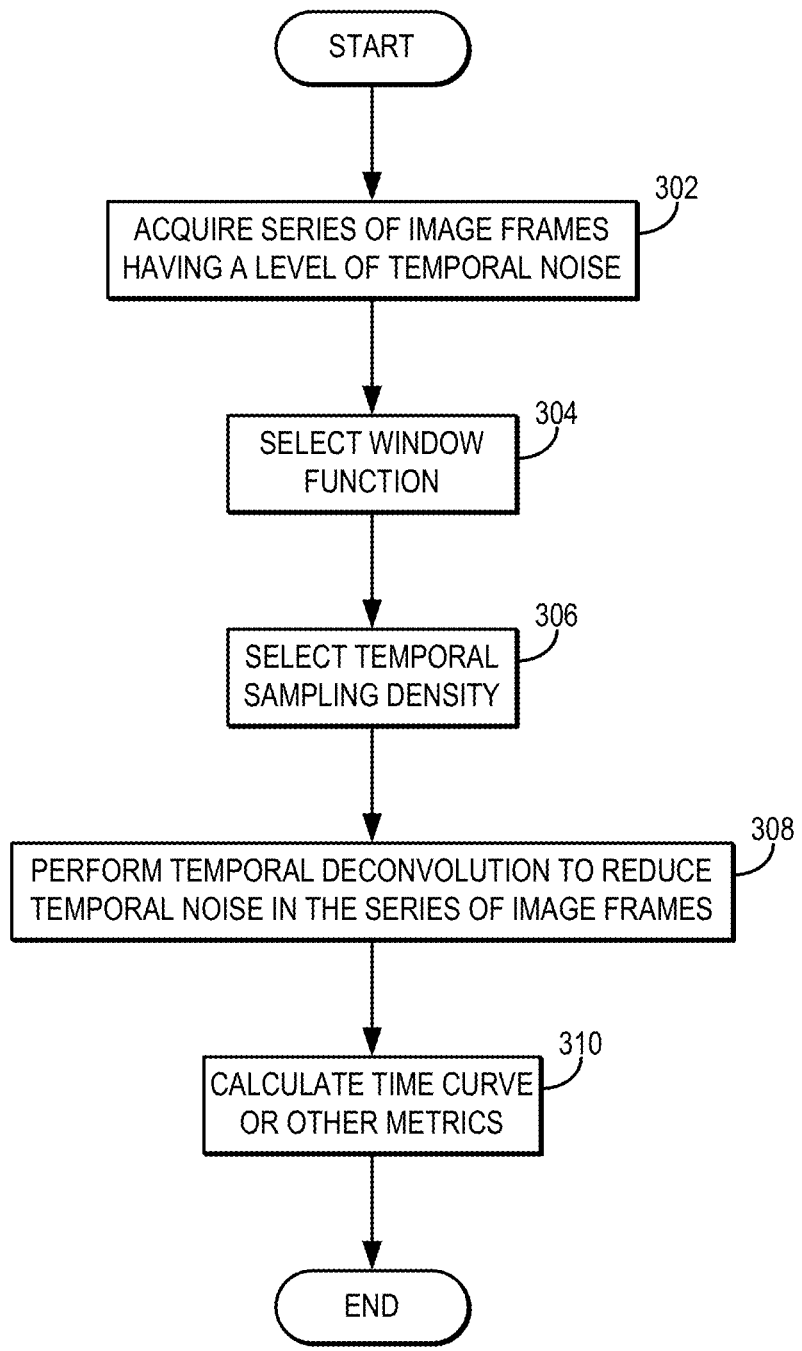
FIG. 3 is a flowchart setting forth the steps of an example of a method for reducing temporal noise in a series of time frames using temporal deconvolution techniques.

Referring now to FIG. 3, a flowchart setting forth the steps of an example of a method for reducing temporal fluctuations, or temporal noise, in a series of time frames obtained with a medical imaging system is illustrated. The method begins with acquiring the series of time frames, as indicated at step 302. By way of example, the time frames may be obtained with a C-arm CBCT system; however, the time frames can also be acquired with an MRI system or other suitable medical imaging system. Next, a window function that is representative of a temporal fidelity window is selected, as indicated at step 304. As described above, the window function may be a box-car sharp window function, or other suitable window function. A temporal sampling density is selected next, as indicated at step 306. This temporal sampling density may be the same as the temporal sampling density of the originally acquired image frames, but will generally be higher than the temporal sampling density of those image frames. Using the acquired time frames, the selected window function, and the selected temporal sampling density, a temporal deconvolution is used to improve the temporal sampling density of the acquired time frames, as indicated at step 308. Particularly, the temporal deconvolution includes solving a minimization problem, whether constrained or unconstrained. As indicated at step 310, after the temporal sampling density of the time frames has been increased, a temporal enhancement curve, or other metrics, can be calculated with increased accuracy as compared to the original time frames.

Figure 4A:
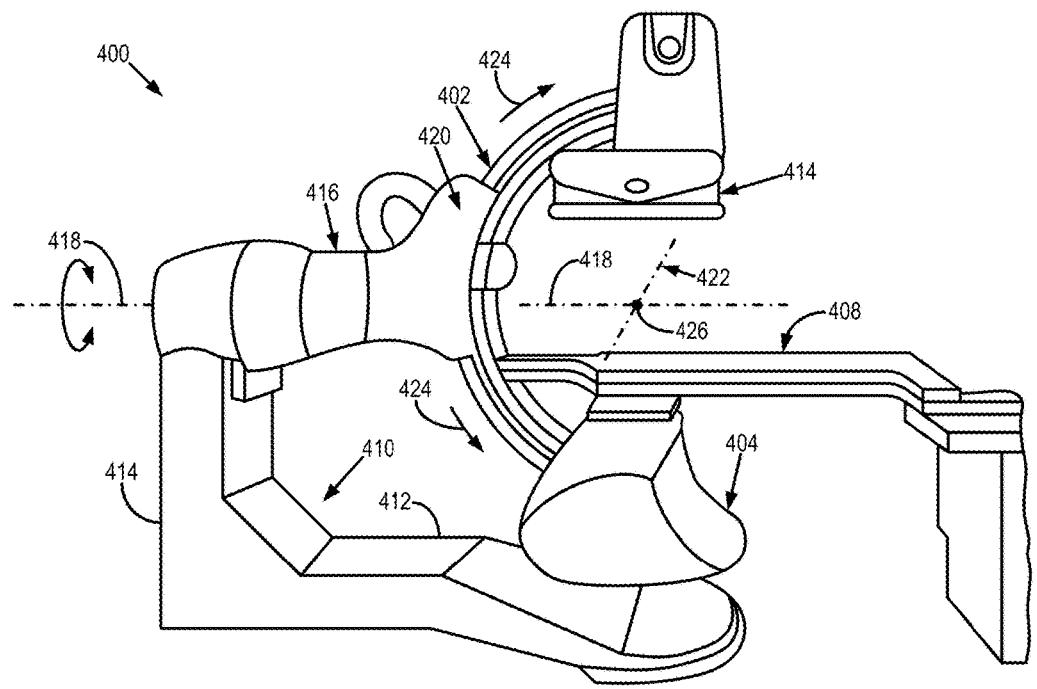
FIGS. 4A and 4B illustrate and example of an x-ray C-arm imaging system.
Figure 4B:
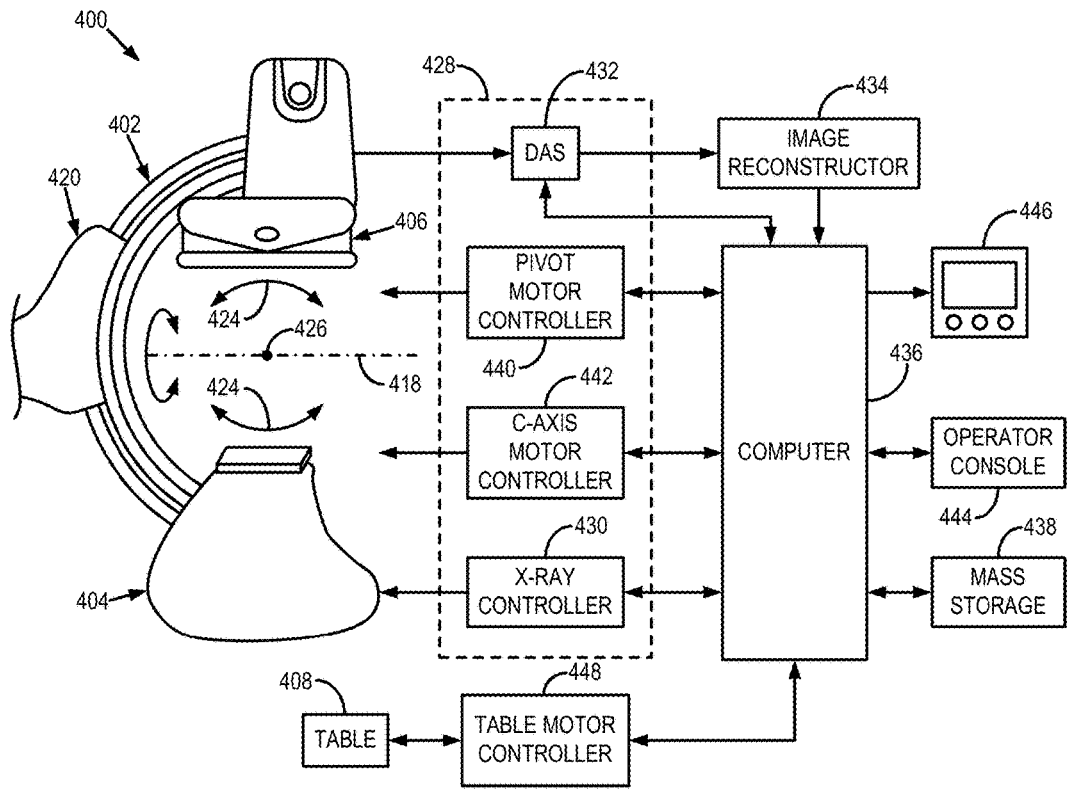

Referring particularly to FIGS. 4A and 4B, an example of a so-called "C-arm" x-ray imaging system 400 is illustrated. Such an imaging system 400 is generally designed for use in connection with interventional procedures. The imaging system 400 is characterized by a gantry having a C-arm 402 that carries an x-ray source assembly 402 on one of its ends and an x-ray detector array assembly 406 at its other end. The gantry enables the x-ray source assembly 403 and detector array assembly 406 to be oriented in different positions and angles around a patient disposed on a table 408, while enabling a physician access to the patient.

The gantry includes a support base 410, which may include an L-shaped pedestal that has a horizontal leg 412 that extends beneath the table 408 and a vertical leg 414 that extends upward at the end of the horizontal leg 412 that is spaced from of the table 408. A support arm 416 is rotatably fastened to the upper end of vertical leg 414 for rotation about a horizontal pivot axis 418. The pivot axis 418 is aligned with the centerline of the table 408 and the support arm 416 extends radially outward from the pivot axis 418 to support a C-arm drive assembly 420 on its outer end. The C-arm 402 is slidably fastened to the drive assembly 420 and is coupled to a drive motor (not shown) that slides the C-arm 402 to revolve it about a C-axis 422, as indicated by arrows 424. The pivot axis 418 and C-axis 422 intersect each other at an isocenter 426 that is located above the table 408 and they are perpendicular to each other.

The x-ray source assembly 404 is mounted to one end of the C-arm 402 and the detector array assembly 406 is mounted to its other end. As will be discussed in more detail below, the x-ray source assembly 404 includes an x-ray source (not shown) that emits a cone beam of x-rays, which are directed at the detector array assembly 406. Both assemblies 404 and 406 extend radially inward to the pivot axis 418 such that the center ray of this cone beam passes through the system isocenter 426. The center ray of the cone beam can, thus, be rotated about the system isocenter 426 around either the pivot axis 418, the C-axis 422, or both during the acquisition of x-ray attenuation data from a subject placed on the table 408.

As mentioned above, the x-ray source assembly 404 contains an x-ray source that emits a cone beam of x-rays when energized. The center ray passes through the system isocenter 426 and impinges on a two-dimensional flat panel digital detector housed in the detector assembly 406. Examples of flat panel detectors include so-called "small flat panel" detectors, in which the detector array panel is around 20×20 centimeters in size. Such a detector panel allows the coverage of a field-of-view of around twelve centimeters. Each detector element produces an electrical signal that represents the intensity of an impinging x-ray and, hence, the attenuation of the x-ray as it passes through the patient. During a scan, the x-ray source and detector array are rotated about the system isocenter 426 to acquire x-ray attenuation projection data from different angles. By way of example, the detector array is able to acquire thirty projections, or views, per second. Generally, the numbers of projections acquired per second is the limiting factor that determines how many views can be acquired for a prescribed scan path and speed.

Referring particularly to FIG. 4B, the rotation of the assemblies 404 and 406 and the operation of the x-ray source are governed by a control mechanism 428 of the imaging system 400. The control mechanism 428 includes an x-ray controller 430 that provides power and timing signals to the x-ray source. A data acquisition system ("DAS") 432 in the control mechanism 428 samples data from detector elements in the detector array and passes the data to an image reconstructor 434. The image reconstructor 434, receives digitized x-ray data from the DAS 432 and performs image reconstruction. The image reconstructed by the image reconstructor 434 is applied as an input to a computer 436, which stores the image in a mass storage device 438 or processes the image further.

The control mechanism 428 also includes pivot motor controller 440 and a C-axis motor controller 442. In response to motion commands from the computer 436, the motor controllers 440 and 442 provide power to motors in the imaging system 400 that produce the rotations about the pivot axis 418 and C-axis 422, respectively. A program executed by the computer 436 generates motion commands to the motor controllers 440 and 442 to move the assemblies 404 and 406 in a prescribed scan path.

The computer 436 also receives commands and scanning parameters from an operator via a console 444 that has a keyboard and other manually operable controls. An associated display 446 allows the operator to observe the reconstructed image and other data from the computer 436. The operator supplied commands are used by the computer 436 under the direction of stored programs to provide control signals and information to the DAS 432, the x-ray controller 430, and the motor controllers 440 and 442. In addition, the computer 436 operates a table motor controller 448, which controls the patient table 408 to position the patient with respect to the system iso center 426.

Figure 5:
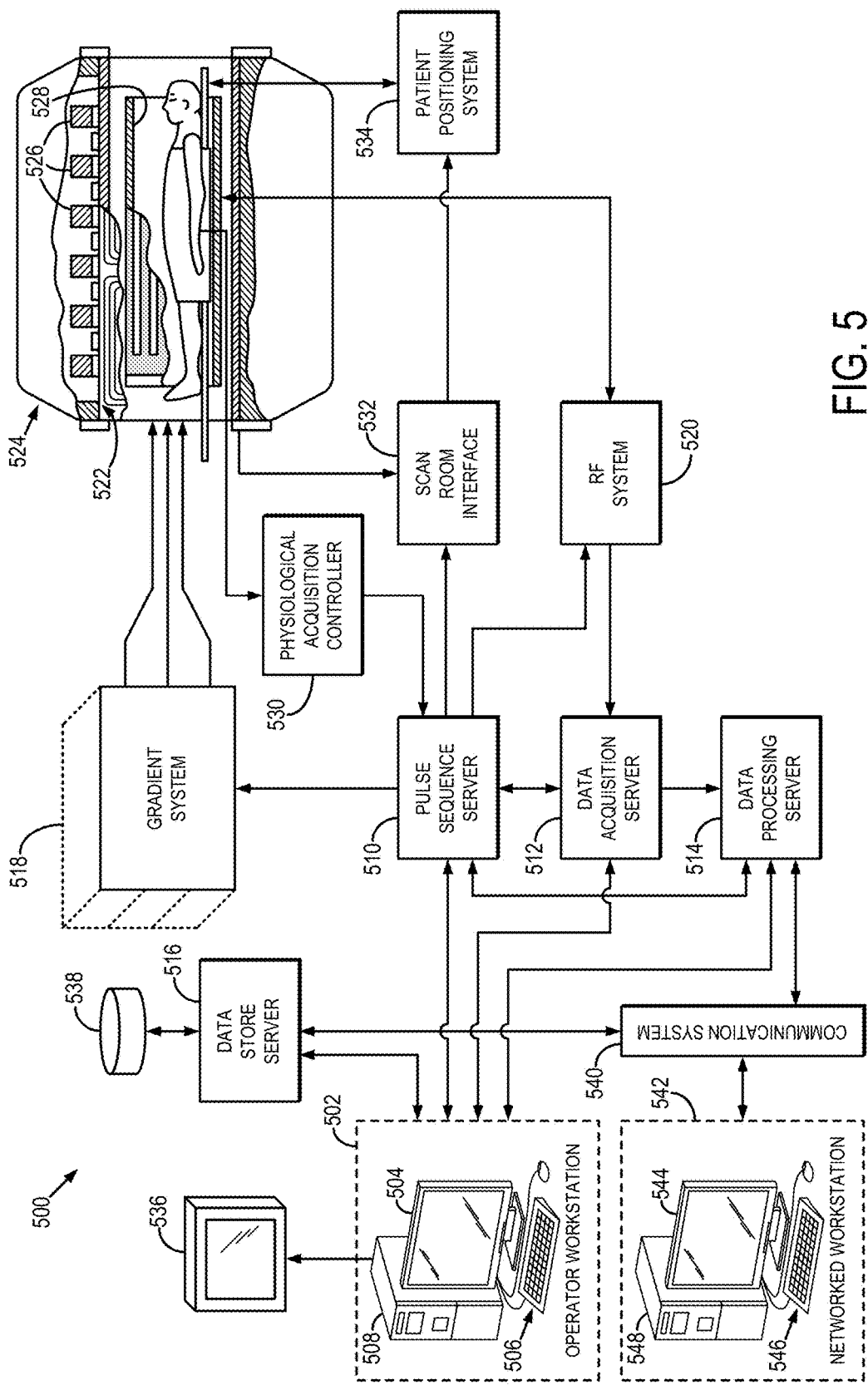
FIG. 5 illustrates a block diagram of an example magnetic resonance imaging system.

Referring particularly now to FIG. 5, an example of a magnetic resonance imaging ("MRI") system 500 is illustrated. The MRI system 500 includes an operator workstation 502, which will typically include a display 504; one or more input devices 506, such as a keyboard and mouse; and a processor 508. The processor 508 may include a commercially available programmable machine running a commercially available operating system. The operator workstation 502 provides the operator interface that enables scan prescriptions to be entered into the MRI system 500. In general, the operator workstation 502 may be coupled to four servers: a pulse sequence server 510; a data acquisition server 512; a data processing server 514; and a data store server 516. The operator workstation 502 and each server 510, 512, 514, and 516 are connected to communicate with each other. For example, the servers 510, 512, 514, and 516 may be connected via a communication system 540, which may include any suitable network connection, whether wired, wireless, or a combination of both. As an example, the communication system 540 may include both proprietary or dedicated networks, as well as open networks, such as the internet.

The pulse sequence server 510 functions in response to instructions downloaded from the operator workstation 502 to operate a gradient system 518 and a radiofrequency ("RF") system 520. Gradient waveforms necessary to perform the prescribed scan are produced and applied to the gradient system 518, which excites gradient coils in an assembly 522 to produce the magnetic field gradients $G_x$, $G_y$, and $G_z$ used for position encoding magnetic resonance signals. The gradient coil assembly 522 forms part of a magnet assembly 524 that includes a polarizing magnet 526 and a whole-body RF coil 528.

RF waveforms are applied by the RF system 520 to the RF coil 528, or a separate local coil (not shown in FIG. 5), in order to perform the prescribed magnetic resonance pulse sequence. Responsive magnetic resonance signals detected by the RF coil 528, or a separate local coil (not shown in FIG. 5), are received by the RF system 520, where they are amplified, demodulated, filtered, and digitized under direction of commands produced by the pulse sequence server 510. The RF system 520 includes an RF transmitter for producing a wide variety of RF pulses used in MRI pulse sequences. The RF transmitter is responsive to the scan prescription and direction from the pulse sequence server 510 to produce RF pulses of the desired frequency, phase, and pulse amplitude waveform. The generated RF pulses may be applied to the whole-body RF coil 528 or to one or more local coils or coil arrays (not shown in FIG. 5).

The RF system 520 also includes one or more RF receiver channels. Each RF receiver channel includes an RF preamplifier that amplifies the magnetic resonance signal received by the coil 528 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M = \sqrt{I^2 + Q^2} \qquad (12);$$

and the phase of the received magnetic resonance signal may also be determined according to the following relationship:

$$\varphi = \tan^{-1}\left(\frac{Q}{I}\right). \qquad (13)$$

The pulse sequence server 510 also optionally receives patient data from a physiological acquisition controller 530. By way of example, the physiological acquisition controller 530 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 510 to synchronize, or "gate," the performance of the scan with the subject's heart beat or respiration.

The pulse sequence server 510 also connects to a scan room interface circuit 532 that receives signals from various sensors associated with the condition of the patient and the magnet system. It is also through the scan room interface circuit 532 that a patient positioning system 534 receives commands to move the patient to desired positions during the scan.

The digitized magnetic resonance signal samples produced by the RF system 520 are received by the data acquisition server 512. The data acquisition server 512 operates in response to instructions downloaded from the operator workstation 502 to receive the real-time magnetic resonance data and provide buffer storage, such that no data is lost by data overrun. In some scans, the data acquisition server 512 does little more than pass the acquired magnetic resonance data to the data processor server 514. However, in scans that require information derived from acquired magnetic resonance data to control the further performance of the scan, the data acquisition server 512 is programmed to produce such information and convey it to the pulse sequence server 510. For example, during prescans, magnetic resonance data is acquired and used to calibrate the pulse sequence performed by the pulse sequence server 510. As another example, navigator signals may be acquired and used to adjust the operating parameters of the RF system 520 or the gradient system 518, or to control the view order in which k-space is sampled. In still another example, the data acquisition server 512 may also be employed to process magnetic resonance signals used to detect the arrival of a contrast agent in a magnetic resonance angiography ("MRA") scan. By way of example, the data acquisition server 512 acquires magnetic resonance data and processes it in real-time to produce information that is used to control the scan.

The data processing server 514 receives magnetic resonance data from the data acquisition server 512 and processes it in accordance with instructions downloaded from the operator workstation 502. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images;

generating functional magnetic resonance images; calculating motion or flow images; and so on.

Images reconstructed by the data processing server 514 are conveyed back to the operator workstation 502 where they are stored. Real-time images are stored in a data base memory cache (not shown in FIG. 5), from which they may be output to operator display 512 or a display 536 that is located near the magnet assembly 524 for use by attending physicians. Batch mode images or selected real time images are stored in a host database on disc storage 538. When such images have been reconstructed and transferred to storage, the data processing server 514 notifies the data store server 516 on the operator workstation 502. The operator workstation 502 may be used by an operator to archive the images, produce films, or send the images via a network to other facilities.

The MRI system 500 may also include one or more networked workstations 542. By way of example, a networked workstation 542 may include a display 544; one or more input devices 546, such as a keyboard and mouse; and a processor 548. The networked workstation 542 may be located within the same facility as the operator workstation 502, or in a different facility, such as a different healthcare institution or clinic.

The networked workstation 542, whether within the same facility or in a different facility as the operator workstation 502, may gain remote access to the data processing server 514 or data store server 516 via the communication system 540. Accordingly, multiple networked workstations 542 may have access to the data processing server 514 and the data store server 516. In this manner, magnetic resonance data, reconstructed images, or other data may exchanged between the data processing server 514 or the data store server 516 and the networked workstations 542, such that the data or images may be remotely processed by a networked workstation 542. This data may be exchanged in any suitable format, such as in accordance with the transmission control protocol ("TCP"), the internet protocol ("IP"), or other known or suitable protocols.

The present invention has been described in terms of one or more preferred embodiments, and it should be appreciated that many equivalents, alternatives, variations, and modifications, aside from those expressly stated, are possible and within the scope of the invention.

The invention claimed is:

1. A computer-implemented method for increasing a temporal fidelity of a series of image frames obtained with a medical imaging system, the steps of the method comprising:
   a) acquiring the series of image frames depicting a time-varying image contrast from in a subject using the medical imaging system and providing the series of image frames to a computer system, wherein the time-varying image contrast is representative of temporal dynamics of a contrast agent present in the subject;
   b) selecting with a computer system, a window function that defines a temporal window that is representative of a temporal fidelity window;
   c) producing with the computer system, another series of image frames having an increased temporal fidelity to the time-varying image contrast as compared to the series of image frames acquired in step a) by performing, with the computer system, a temporal deconvolution on the series of image frames acquired in step a) using the window function selected in step b).

2. The method as recited in claim 1 in which step c) includes performing the temporal deconvolution with the computer system by performing a minimization using an objective function that includes the series of image frames acquired in step a) and the window function selected in step b).

3. The method as recited in claim 1 in which the medical imaging system is at least one of a C-arm cone beam computed tomography system, a cone beam computed tomography system having a digital detector, and a digital tomosynthesis imaging system.

4. The method as recited in claim 1 further comprising computing, with the computer system, a time enhancement curve that represents the temporal dynamics of the contrast agent from the another series of image frames produced in step c).

5. The method as recited in claim 1 in which the medical imaging system is a magnetic resonance imaging system and the time-varying image contrast is related to at least one of a longitudinal relaxation rate, a transverse relaxation rate, and temporal dynamics of the contrast agent present in the subject.

6. A computer-implemented method for increasing a temporal sampling density of a series of image frames obtained with a medical imaging system, the steps of the method comprising:
   a) acquiring the series of image frames at a first temporal sampling density using the medical imaging system;
   b) selecting with a computer system, a window function defines a temporal window that is representative of a temporal fidelity window;
   c) selecting with the computer system, a second temporal sampling density that is higher than the first temporal sampling density;
   d) producing with the computer system, another series of image frames having the second temporal sampling density by performing, with the computer system, a temporal deconvolution on the series of image frames acquired in step a) using the window function selected in step b) and the second temporal sampling density selected in step c).

7. The method as recited in claim 6 in which step d) includes performing the temporal deconvolution with the computer system by performing a minimization using an objective function that includes the series of image frames acquired in step a), the window function selected in step b), and the second temporal sampling density selected in step c).

8. A computer-implemented method for reducing temporal noise in a series of image frames obtained with a medical imaging system, the steps of the method comprising,
   a) acquiring the series of image frames having a level of temporal noise using the medical imaging system;
   b) selecting with a computer system, a window function that defines a temporal window that is representative of a temporal fidelity window;
   c) selecting with the computer system, a temporal sampling density;
   d) producing with the computer system, another series of image frames having reduced temporal noise as compared to the series of image frames acquired in step a) by performing, with the computer system, a temporal deconvolution on the series of image frames acquired in step a) using the window function selected in step b) and the temporal sampling density selected in step c).

9. The method as recited in claim 8 in which step d) includes performing the temporal deconvolution with the computer system by performing a minimization using an objective function that includes the series of image frames acquired in step a), the window function selected in step b), and the temporal sampling density selected in step c).

10. The method as recited in claim 8 in which the temporal sampling density selected in step c) is different than a temporal sampling density of the series of image frames acquired in step a).

11. The method as recited in claim 10 in which the temporal sampling density selected in step c) is higher than the temporal sampling density of the series of image frames acquired in step a).

* * * * *